(12) United States Patent
Kearney et al.

(10) Patent No.: US 6,616,327 B1
(45) Date of Patent: Sep. 9, 2003

(54) FRACTAL STACK FOR SCALING AND DISTRIBUTION OF FLUIDS

(75) Inventors: Michael M. Kearney, Twin Falls, ID (US); Kenneth R. Peterson, Twin Falls, ID (US); Michael W. Mumm, Hansen, ID (US)

(73) Assignee: Amalgamated Research, Inc., Twin Falls, ID (US)

( * ) Notice: Subject to any disclaimer, the term of this patent is extended or adjusted under 35 U.S.C. 154(b) by 0 days.

(21) Appl. No.: 09/668,913

(22) Filed: Sep. 25, 2000

Related U.S. Application Data (63) Continuation of application No. PCT/US99/06245, filed on Mar. 22, 1999.
(60) Provisional application No. 60/079,028, filed on Mar. 23, 1998.

(51) Int. Cl.[7] .................................................. B01F 5/06
(52) U.S. Cl. ........................................ 366/340; 366/341
(58) Field of Search ................................ 366/336, 337, 366/338, 339, 340, 341, 342, 349, 174.1, 183.1; 137/625.28, 599; 165/109.1, 159, 172, 296, 100, 102; 138/44; 210/198.2

(56) References Cited

U.S. PATENT DOCUMENTS

| | | | | |
|---|---|---|---|---|
| 1,409,259 A | * | 3/1922 | Sykora | |
| 2,734,224 A | * | 2/1956 | Winstead | |
| 3,533,594 A | * | 10/1970 | Seguller | |
| 4,354,932 A | * | 10/1982 | McNeil | 210/198.2 |
| 4,537,217 A | * | 8/1985 | Allen, Jr. | 137/561 A |
| 4,550,681 A | * | 11/1985 | Zimmer et al. | |
| 4,999,102 A | * | 3/1991 | Cox et al. | 138/44 |
| 5,289,224 A | * | 2/1994 | Devaney, Jr. et al. | 354/324 |
| 5,296,375 A | * | 3/1994 | Kricka et al. | 435/2 |
| 5,304,487 A | | 4/1994 | Wilding et al. | |
| 5,354,460 A | * | 10/1994 | Kearney et al. | 210/198.2 |
| 5,355,318 A | * | 10/1994 | Dionnet et al. | 364/468 |
| 5,486,335 A | * | 1/1996 | Wilding et al. | |
| 5,584,996 A | | 12/1996 | Petit | |
| 5,938,333 A | * | 8/1999 | Kearney | 366/336 |

FOREIGN PATENT DOCUMENTS

| | | |
|---|---|---|
| WO | WO 98/14268 | 4/1998 |

\* cited by examiner

*Primary Examiner*—Tony G. Soohoo
(74) *Attorney, Agent, or Firm*—TraskBritt

(57) ABSTRACT

Fluid transporting fractal devices, which can be employed whenever a controlled distribution and/or collection of fluids is desired, are constructed to position fractal stages of either progressively smaller or progressively larger scales along the direction of flow (Plates #1–#8). A preferred construction assigns generations of recursive fractal pattern to plates arranged in a stack.

12 Claims, 8 Drawing Sheets

FRACTAL STACK FOR SCALING AND DISTRIBUTION OF FLUIDS

This is a continuation of PCT/US99/06245 filed Mar. 22, 1999, and application claims the benefit of U.S. Provisional Application No. 60/079,028 filed Mar. 23, 1998.

TECHNICAL FIELD

This invention pertains to the scaling and distribution of fluids. It provides fractal structures arranged to minimize the intersection of recursive fluid flow paths.

BACKGROUND ART

Fluid transporting fractal structures ("fractals") have recently become available for the control of fluid flow. U.S. Pat. No. 5,354,460, the disclosure of which is incorporated by reference herein, describes a fractal structure embodied as a fluid distributor/collector. A notable characteristic of the device disclosed by the '460 patent is its recursive scaling configuration which is, for purposes of this disclosure, regarded as a "fractal." This fractal configuration provides exceptionally even fluid flow distribution.

PCT/US97/17516, the disclosure of which is incorporated by reference herein, describes the use of space filling fluid transporting fractals for use as alternatives to the scaling and distribution function of turbulence.

"Fractal scaling," as contemplated by this invention, is a recursive process by which an algorithm is applied in successive stages, each time to process the outputs from an immediately preceding stage. A simple case for purposes of illustration is to apply the algorithm "divide a flow stream into two equal flow streams." According to this example, a flowing stream is divided into two equal streams of half the initial volume during a first stage. Each of the two resulting streams is then similarly divided to produce a total of four equal streams of reduced volume in a second stage. Those four resulting streams are then divided into eight equal streams of reduced volume in a third stage, and so on, through as many stages as are desired to achieve the distribution of fluid flow required for a particular application.

Mathematical models of fractal geometry assume that each division at each stage is identical and that precisely identical geometry is followed through each branch of successive sages. In practice, it is recognized that absolute adherence to a mathematical model is impractical. Accordingly, fractal devices are usually constructed to approximate a theoretical model. That is, because of manufacturing and space constraints, commercial fractals often make use of "similar," rather than "identical" fractal patterns. This disclosure should be understood within that context. The practical consequences of this departure from theoretical are generally minimal within the practical realm.

DISCLOSURE OF INVENTION

The present invention comprises an improved fluid transporting fractal. Devices constructed in accordance with this invention can be employed whenever a controlled distribution and/or collection of fluids is desired. A notable feature of the structures of this invention is the positioning of fractal stages along the direction of flow. That is, stages of either progressively smaller or progressively larger scales are arranged serially in the direction of flow. It is within contemplation to construct an entire device, or multi-stage segment of such a device, as a unitary structure, e.g., through investment, shell or lost wax casting techniques. The multi level fractals of this invention are more conveniently provided, however through the use of a stack of fractal elements in an assembly, or "fractal stack." To avoid redundancy of description, this disclosure gives primary emphasis to fractal stacks utilized as distributors.

The individual elements of a typical fractal stack are three-dimensional components, structured and arranged for juxtaposed assembly in a specified sequence. Each fractal element is provided with channels and ports constituting a portion of a fractal fluid scaling array. Various portions of the scaling array may be assigned to individual elements, those portions being selected such that a practical recursive fractal array results from the assembly of the elements, in proper sequence, into the fractal stack. A presently preferred arrangement assigns the fluid flow channels of a specified fractal stage to a single specified fractal element. It is within contemplation to assign channels of different fractal stages to a single fractal element, and it is also within contemplation to divide channels of a specified fractal stage among a plurality of fractal elements. The channels associated with a particular element may be positioned on a single side or on the opposed sides. In the latter case, the channels of a fractal stage may be defined by juxtaposed matching grooves at the interfaces between adjacent elements.

An exemplary fractal element has a relatively large cross section normal the direction of fluid flow, to accommodate the largest fractal pattern in the stack. This pattern is typically that of the final fractal stage, and its "footprint" is dependant upon (among other things) the fractal number (the number of stages) accommodated by the stack. A relatively small height dimension is required to accommodate the flow channels arranged in a fractal pattern within, (most often openly communicating with either or both interfacing surfaces of the element). Such elements take the form of short prisms, usually cylindrical, and are designated "fractal plates," for purposes of this disclosure. Fractal plates may be stacked upon one another such that fractal distribution to progressively smaller scales occurs as fluid passes through the stack. The device therefore acts as a fluid distributor. The structures of this invention may alternatively be utilized as a fluid collector. For such applications, fluid is caused to pass from the smallest to the largest fractal scale. Near limitless scaling of fluid motion can be accomplished with this invention by the addition of fractal plates to the stack, that is, by increasing the fractal number of the stack.

According to certain embodiments of this invention, a "finishing" structure, such as a plate or plates, may be added to the fractal stack to provide additional fluid scaling. This final scaling stage is beneficial when the fractal manufacturing techniques used on the larger scale plates reaches a practical limit. The finishing plate allows a final fluid scaling to be implemented at the smallest of scales. The finishing plate can be of any material or configuration which provides a scaling effect. For example, fins, corrugations, column packings, screens, sponges or other structures capable of providing a tortuous, (or mixing-type), path for the fluid exiting the final fractal pattern can be used for this purpose. Fluid collision or impinging structure can also be used for the finishing plate. For example, small obstructions may be positioned in the path of the final fluid exits. Fluid splashing against these structures is broken into streams or droplets of smaller scales, thereby undergoing a final scaling effect.

The invention is thus applied in practice to a fractal fluid flow system in which recursive flow paths are arranged in a fractal pattern including generations of progressively increasing or decreasing scale. The improvement of the invention generally comprises providing portions of the fractal pattern in stacked arrangement with respect to each other, whereby to avoid intersection of recursive flow channels. The generations of progressively increasing or decreasing scale are typically positioned between an inlet and an outlet, whereby to modify the scale of fluid flow through the system. The present invention arranges successively such generations of structural flow channels at different distances from the inlet in the direction of the outlet.

Most often, portions of the fractal pattern are provided on structural elements assembled in stacked arrangement with respect to each other. The structural elements are typically approximately congruent geometric solids with flow channels arr. The invention is thus applied in practice to a fractal fluid flow system in which recursive flow paths are arranged in a fractal pattern including generations of progressively increasing or decreasing scale. The improvement of the invention generally comprises providing portions of the fractal pattern in stacked arrangement with respect to each other, whereby to avoid intersection of recursive flow channels. The generations of progressively increasing or decreasing scale are typically positioned between an inlet and an outlet, whereby to modify the scale of fluid flow through the system. The present invention arranges successively such generations of structural flow channels at different distances from the inlet in the direction of the outlet. Anged in conformance to the fractal pattern so as to constitute fractal elements. Ideally, these fractal elements comprise plates, which contain fractal patterns, stacked, one upon another, to provide a fractal stack constituting means for the distribution of fluid to progressively different scales as fluid is caused to pass through the stack from its inlet to its outlet. The inlet may be located to direct fluid to either the largest or smallest scale fractal generation.

Particularly when the stack is operated as a distributor, it may include finishing structure at one (outlet) end, structured and arranged to promote even distribution of fluid normal the direction of fluid low through the stack. The finishing structure is preferably constructed and arranged to provide multiple channel tortuous pathways for fluid exiting the fractal pattern. The opposite (inlet) end of the stack may comprise a structural element containing distribution channels arranged to receive fluid from a primary inlet and to distribute scaled quantities of that fluid to respective inlets of a first generation of the fractal pattern.

Another embodiment of this invention provides open area around the fractal pattern of the plates so that fluids can flow through the bulk of the device in either direction without interfering with the scaling of the fluid inside the fractal. This arrangement is useful for applications such as counter-current operation or when a fluid is to be introduced or taken from a stream of fluid passing through the stack.

Because fractals are, by definition, invariant to scaling, this invention can be used for any size application and still provide any desired range of fluid scaling. This device theoretically enables infinite scaling of fluids. The existing limits on manufacturing objects of very large or very small size impose practical limits upon sizing at present. It is understood, however, that as manufacturing methods for constructing large or small objects improve, those methods can be applied to expand the practical range of scaling offered by this invention.

BEST MODES FOR CARRYING OUT THE INVENTION

Figure 1:
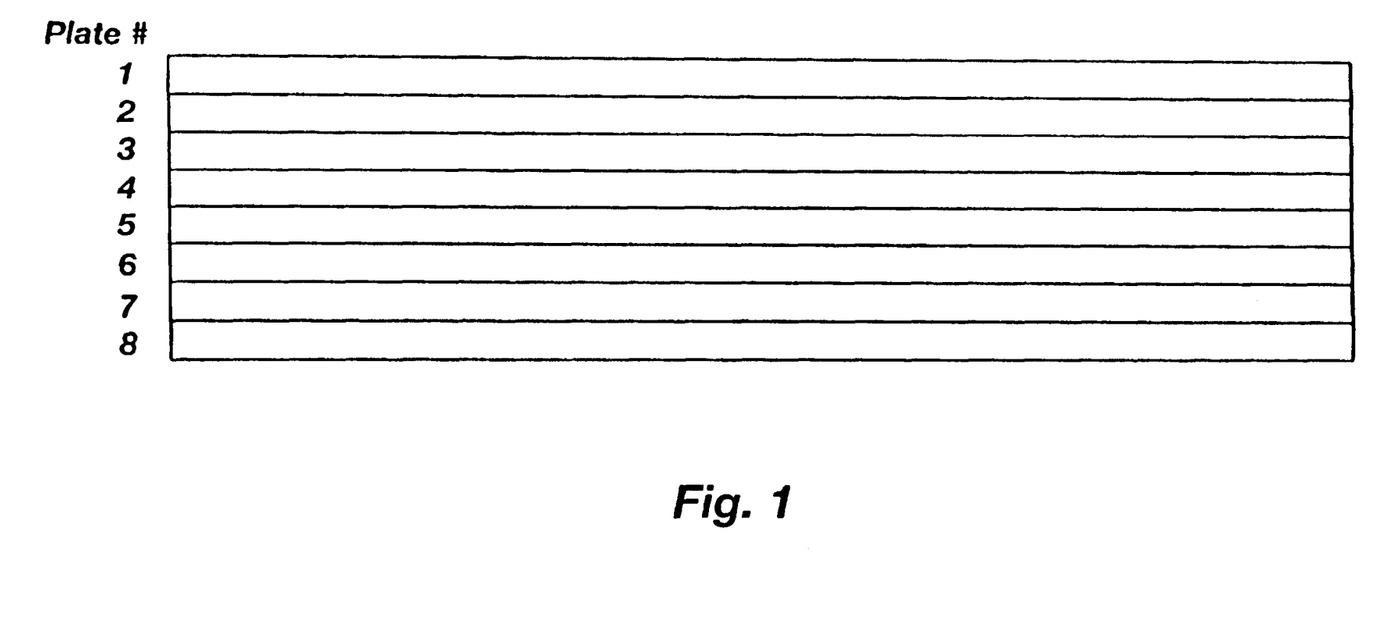
FIG. 1 is a view in side elevation, illustrating a fractal stack comprising eight plates.
Figure 2:
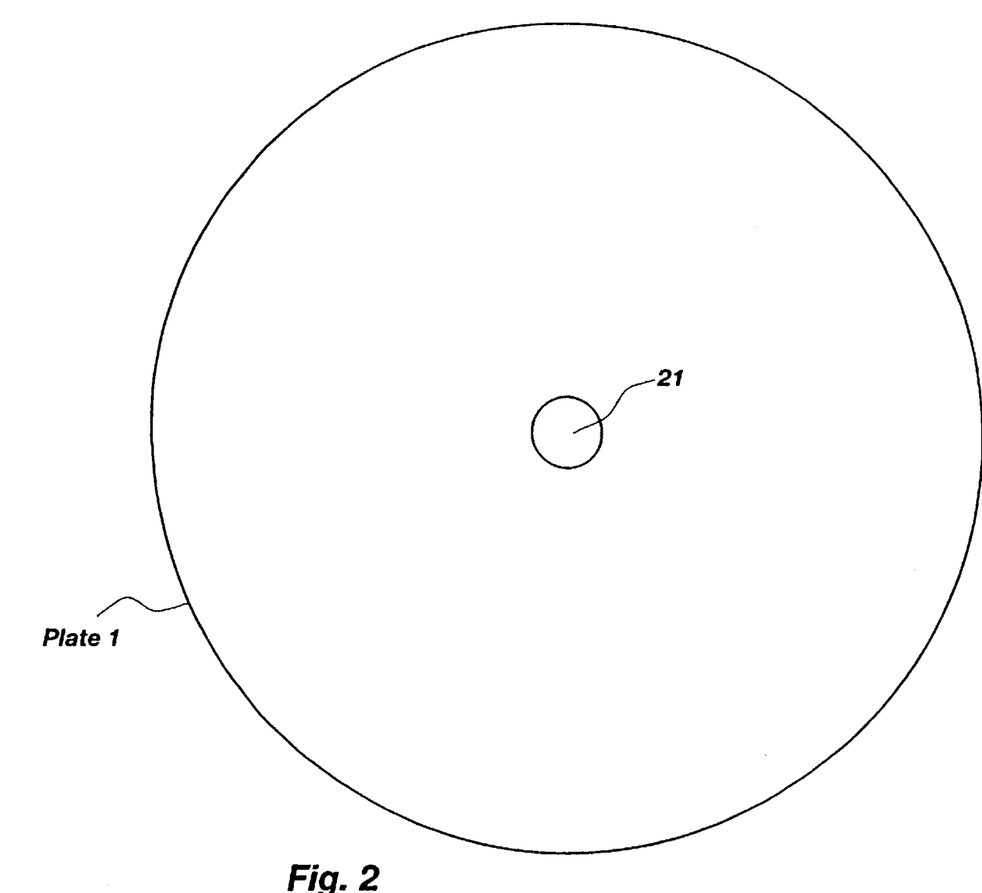
FIG. 2 is a top plan view of Plate 1 of FIG. 1.
Figure 3:
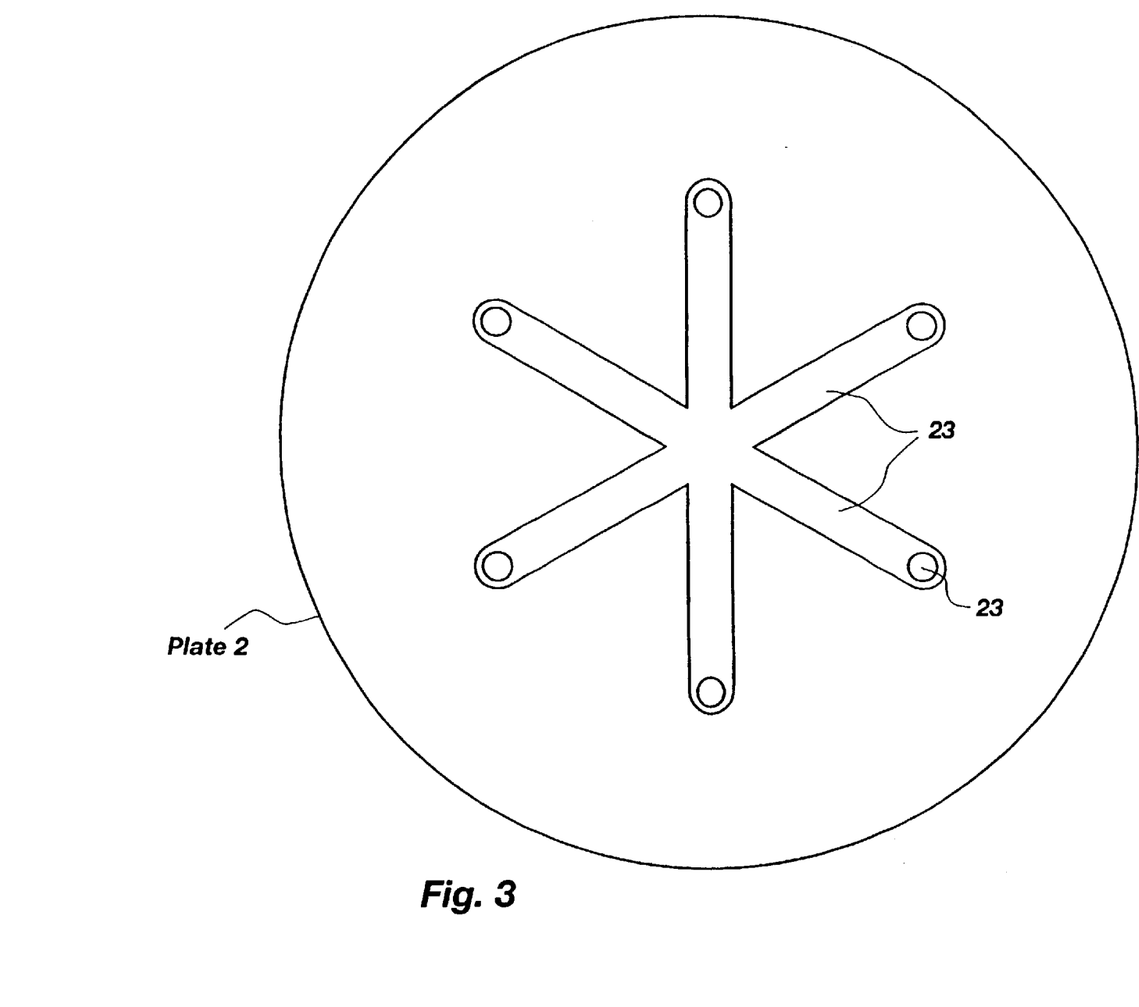
FIG. 3 is a top plan view of Plate 2 of FIG. 1.
Figure 4:
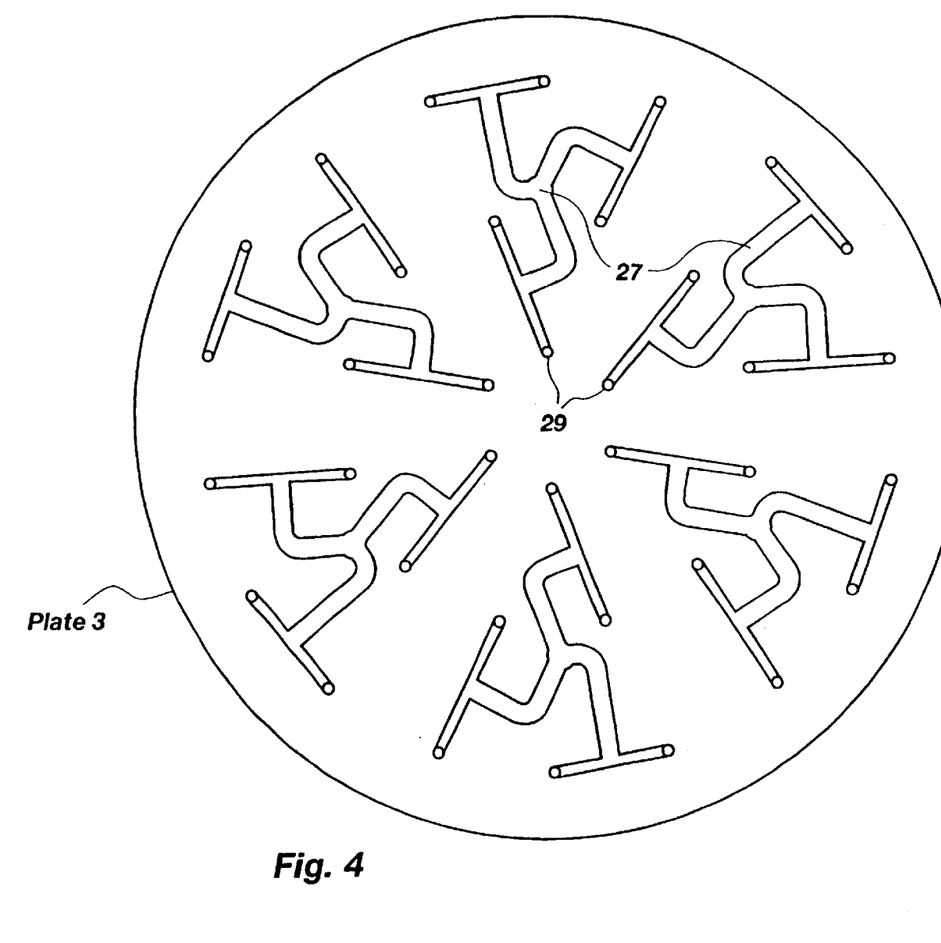
FIG. 4 is a top plan view of Plate 3 of FIG. 1.

The fractal stack illustrated by FIG. 1 includes eight plates, although the invention contemplates embodiments having either fewer or more plates, depending upon the requirements of a particular application. As illustrated, circular ports pass through the plates, and elongate channels between inlet and outlet ports comprise grooves cut, molded or otherwise formed in one surface of the plate. Plates 1–3 provide a general preliminary scaling of the fluid introduced to the inlet 21 (FIG. 2) and divided through channels 23 to ports 25 (FIG. 3) and then through channels 27 to ports 29 (FIG. 4). Plate 3 provide a 6-way conduit scaling of the fluid introduced to the inlet 21. Plate 3 provides a 36-way conduit scaling of the fluid. Plates 4, 5, 6, and 7 are fractal elements, which allow the near limitless scaling of this invention. (See FIGS. 5 and 6.) Any number of fractal plates can be used, depending upon the fine scaling requirements of the application at hand. Only four such plates are illustrated. Plate 8 represents an optional "finishing" plate.

Figure 5:
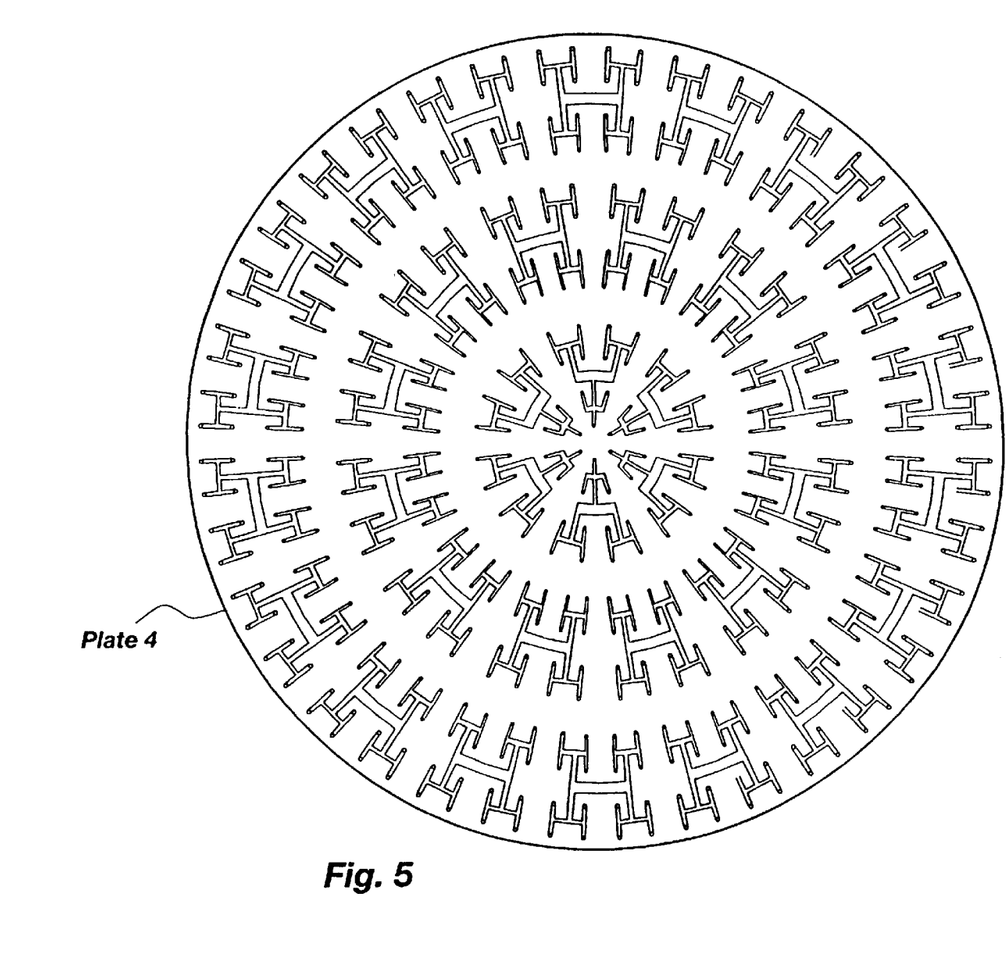
FIG. 5 is a top plan view of Plate 4 of FIG. 1.

Plate 4 (FIG. 5) is the first fractal scaling plate in the illustrated system. In designing a system, conduit plates (1, 2 and 3) preceding the fractal plates (4, 5, 6, and 7) can be modified with respect to number and pattern as required to coordinate liquid feed to the subsequent fractal plates. For example, FIG. 5 shows 3 rings of fractal pattern. Because of space limitations, the fractal pattern of the innermost ring differs somewhat from that of the outer two rings. Adding additional rings, e.g., for larger diameter devices, will require a larger number of conduit branches on the previous non-fractal scaling plate or plates. It can also be seen from FIG. 5 that additional fractal scaling pattern may be provided on any fractal plate before passing the fluid to the next plate in the series. It is not usually necessary to pass fluid to the next plate until a crossover of the fractal conduit pattern is imminent.

Figure 6:
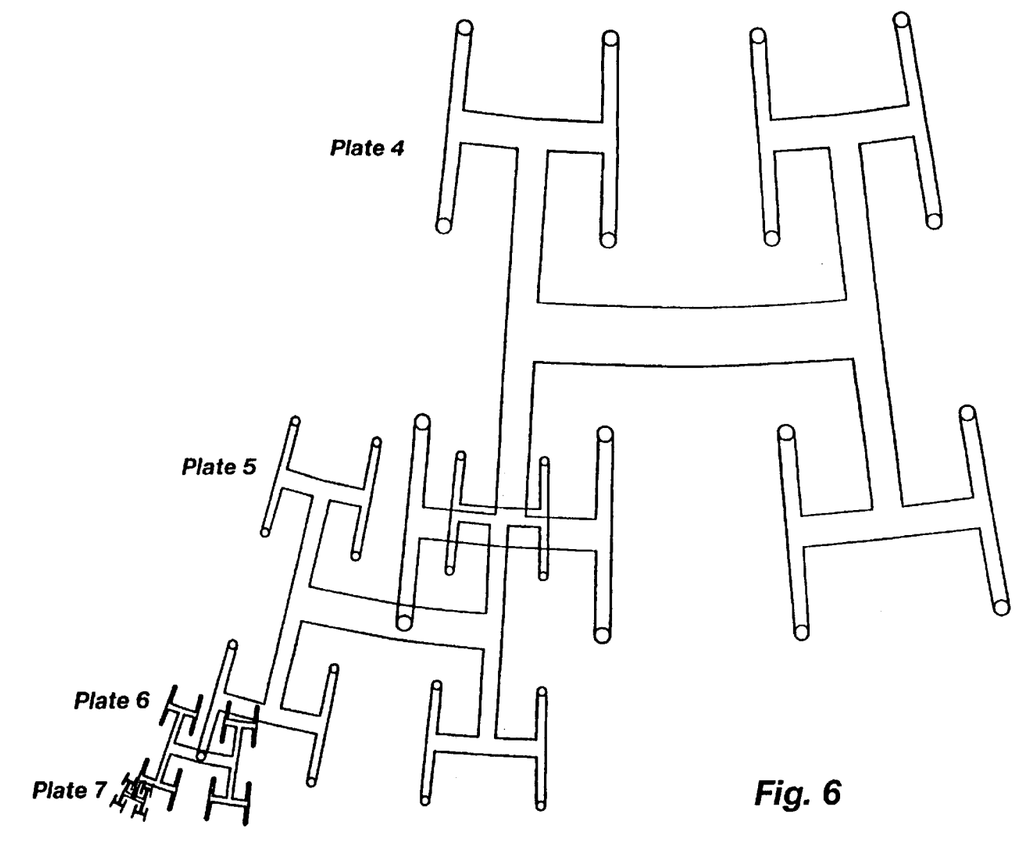
FIG. 6 is a diagram illustrating the fractal pattern effected by plates 4, 5, 6 and 7 of FIG. 1.

FIG. 6 illustrates the basic fractal flow distribution pattern provided through plates 4, 5, 6 and 7. Scaling of the fluid can continue without limit (within manufacturing constraints) by adding additional fractal plates to the stack (FIG. 1). FIG. 6 shows that individual fluid conduits would inevitably overlap were the entire pattern of fluid conduits placed on a single plate.

Figure 7:
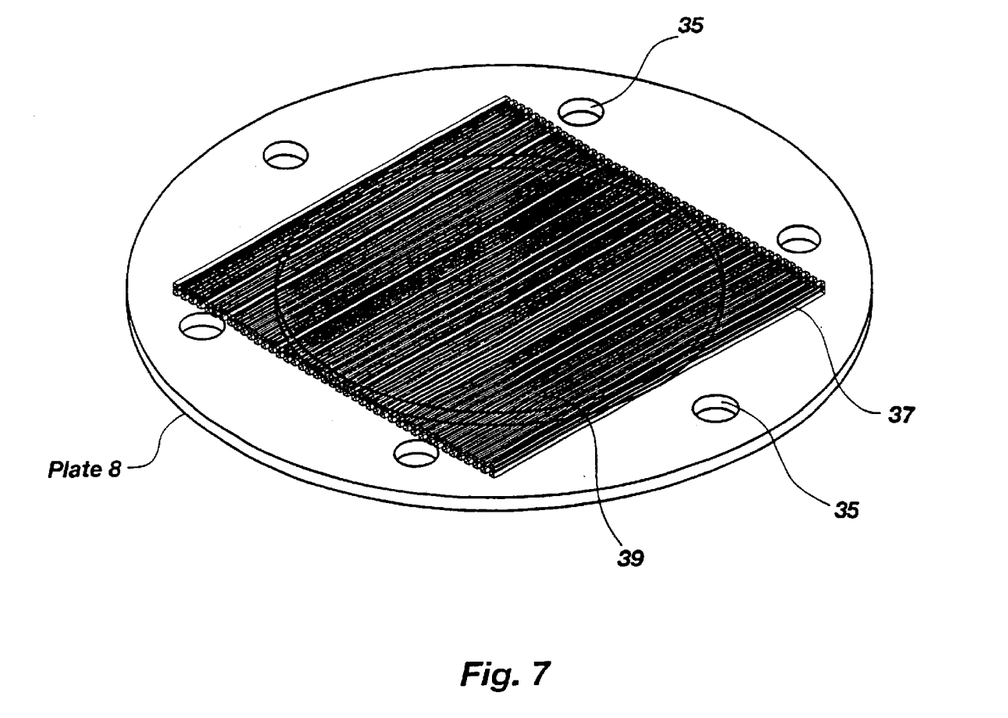
FIG. 7 is a pictorial view of Plate 8 of FIG. 1.
Figure 8:
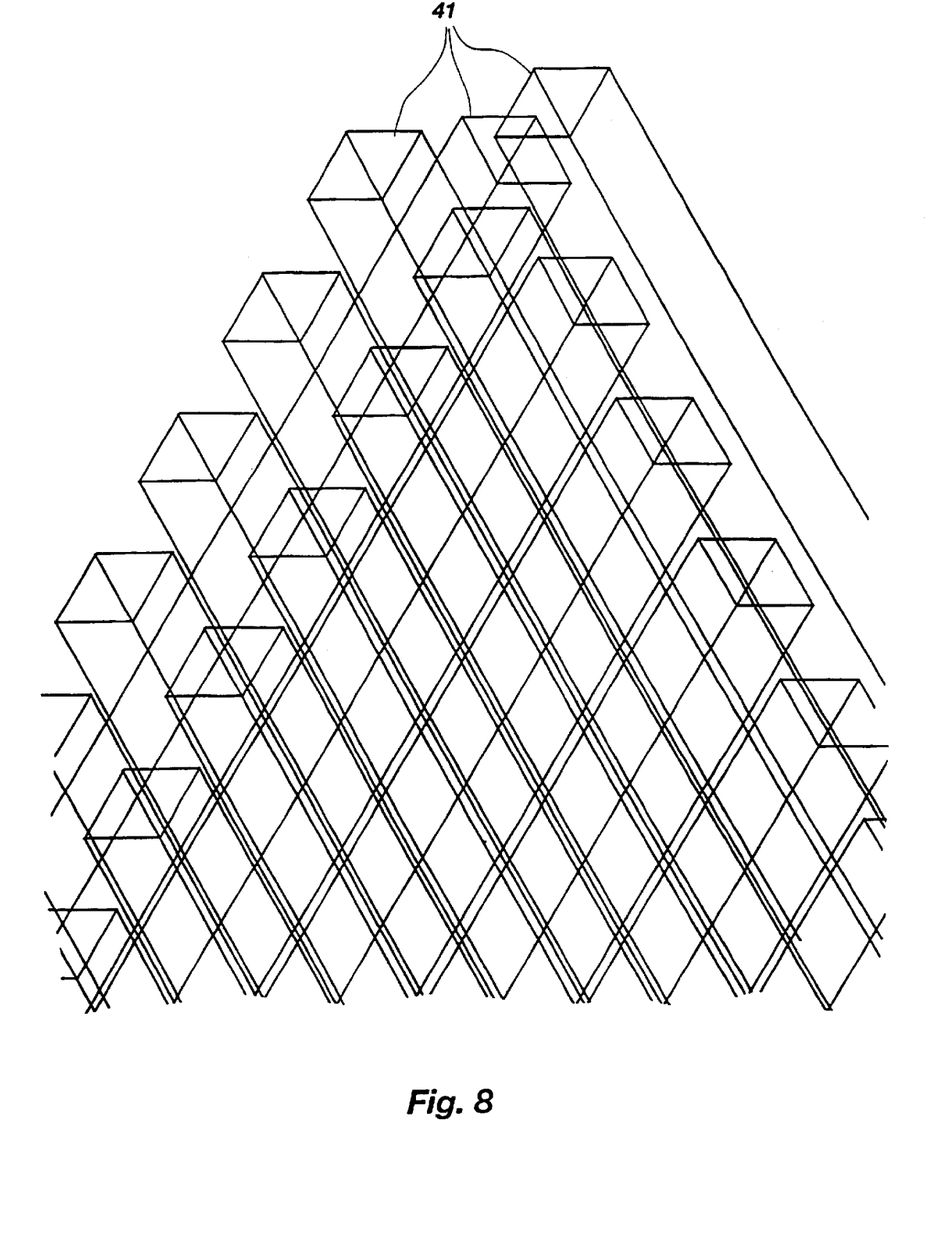
FIG. 8 is an enlarged pictorial view of a portion of FIG. 7.

FIG. 7, while illustrating a finishing plate, also illustrates pictorially the general shape and relative dimensions of all of the plates in the stack. Bolt holes 35 are provided in each of the plates for connecting them in position within the fractal stack. A structural element 37 is positioned atop a fluid exit port 39. As best shown by the enlarged 25 depiction of FIG. 8, the element 37 is constructed of bars 41, arranged to provide a final tortuous pathway, which finishes spreading of the fluid evenly over the cross section of the stack.

INDUSTRIAL APPLICABILITY

Devices constructed in accordance with this invention can be employed whenever a controlled distribution and/or collection of fluids is desired.

Any fluid process may benefit from this invention if control of fluid scaling is advantageous. Without limiting the scope of the appended claims in any way, exemplary applications of the invention include: general scaling of fluids from large to smaller scale motion; general scaling of fluids from small to larger scale motion; rapid formation of fluid surfaces; rapid formation of low-turbulence fluid surfaces; rapid collection of fluid surfaces. Apparatus constructed in accordance with this invention may, among other things, be applied to the introduction of low turbulence fluid surfaces into other fluids; adsorption or absorption processes; chromatography procedures; ion exchange operations; gas/liquid counter-current applications; distillation equipment; reactors; aerators and flow through mixers. While the foregoing examples are expressed in terms of "motion" and "surfaces," they may also be conceptualized in terms of fluid volumes or streams.

What is claimed is:

1. A fractal fluid flow system comprising:
   a plurality of first plates, each said first plate defining a plurality of recursive flow paths, each recursive flow path having a flow inlet which defines a longitudinal axis and at least three flow outlets arranged symmetrically and two dimensionally about said longitudinal axis in a plane perpendicular to said longitudinal axis, each said recursive flow path being isolated from flow communication with the remaining said recursive flow paths in said first plate, said plurality of first plates being arranged adjacently in a stacked array to define a fractal pattern, each said recursive flow path in each said first plate being positioned in flow communication with an outlet of a said recursive flow path of an upstream first plate positioned adjacent thereto and each said outlet of a said recursive flow path being in flow communication with a respective said inlet of a respective recursive flow path of a downstream first plate positioned adjacently thereto, each said first plate including a generation of flow paths of progressively increasing scale in relation to the recursive flow path of an upstream first plate positioned adjacent thereto, said plurality of first plates defining a primary fluid flow pathway direction through said stacked array and a distribution of said flow over a cross section oriented orthogonal to said primary fluid flow pathway direction;
   a proximal plate positioned adjacent said stacked array, said proximal plate defining an initial flow path positioned in flow communication with said recursive flow paths in a first outer first plate for introducing a fluid flow into said stacked array; and
   a distal plate positioned adjacent said stacked array, said distal plate, defining a final flow path, positioned in flow communication with said recursive flow paths in a second outer first plate, said distal plate having a plate face which defines a plurality of outlets in flow communication with said final flow paths, said outlets being evenly distributed over a plate face surface having a dimensional area substantially equal to an area of said cross section of said stacked arrangement, said outlets being oriented for evenly distributing said fluid flow, exiting said outlets, over an area dimensionally corresponding to an area of said cross section.

2. The fractal flow system of claim 1, further including a finishing structure positioned proximate said distal plate to function as a distributor, whereby to promote even distribution of said fluid normal the direction of flow of said fluid.

3. The fractal flow system of claim 2, wherein said finishing structure is constructed and arranged to provide multiple channel tortuous pathways for fluid exiting said fractal pattern.

4. In a fractal fluid flow system in which recursive generations of structural flow channels are arranged in a fractal pattern including generations of progressively increasing scale between an inlet and an outlet, whereby to modify the scale of fluid flow through the system, the improvement comprising arranging said recursive generations of structural flow channels in a stacked arrangement of at least three plates at different distances from said inlet in the direction of said outlet for distributing said fluid flow evenly over a cross section of said stacked arrangement, wherein each said plate defines a plurality of flow paths which are physically isolated from one another within said plate, thereby avoiding an intersection of individual flow paths within each plate, wherein said cross section is defined as being oriented orthogonal to a primary direction of fluid flow through said system wherein each individual flow path in each said plate includes a flow inlet and at least three flow outlets, wherein said at least three flow outlets are disposed substantially symmetrically and two dimensionally about a longitudinal axis of said flow inlet in a plane perpendicular to said longitudinal axis.

5. An improvement according to claim 4, wherein said fractal pattern is distributed among structural fractal elements arranged in stacked relationship.

6. An improvement according to claim 5, wherein said fractal elements are arranged in a fractal stack with an inlet at a first end of said stack and an outlet at a second end of said stack.

7. An improvement according to claim 6, wherein said first end of said stack comprises a structural element containing distribution channels arranged to receive fluid from said inlet and to distribute scaled quantities of said fluid to respective inlets to a first generation of said fractal pattern.

8. An improvement according to claim 6, further including finishing structure at said output end of a said stack operated to function as a distributor, whereby to promote even distribution of said fluid normal the direction of flow of said fluid.

9. An improvement according to claim 8, wherein said finishing structure is constructed and arranged to provide multiple channel tortuous pathways for fluid exiting said fractal pattern.

10. An improvement according to claim 9, wherein said first end of said stack comprises a structural element containing distribution channels arranged to receive fluid from said inlet and to distribute scaled quantities of said fluid to respective inlets to a first generation of said fractal pattern.

11. A fractal fluid flow system comprising:
    a plurality of first plates, each said first plate defining a plurality of recursive flow paths, each said recursive flow path being physically isolated from the remaining said recursive flow paths in said first plate, each said recursive flow path having a flow inlet and at least three flow outlets which are arranged symmetrically about a longitudinal axis of said flow inlet in a plane oriented perpendicular to said longitudinal axis, said plurality of first plates being arranged adjacently in a stacked array to define a fractal pattern, each said recursive flow path of each said first plate being positioned in flow communication with a respective said outlet of a said recursive flow path of an upstream first plate positioned adjacent thereto and each outlet of said recursive flow path being positioned in flow communication with a respective said inlet of a said recursive flow path of a downstream first plate positioned adjacently thereto, each said first plate including a generation of recursive flow paths of progressively decreasing scale in relation to the recursive flow path of an upstream first plate positioned adjacent thereto, said plurality of first plates defining a primary fluid flow pathway direction through said stacked array and a distribution over a cross section oriented perpendicular to said primary fluid flow pathway direction;

a proximal plate positioned adjacent said stacked array, said proximal plate defining a plurality of initial flow inlets positioned uniformly over a plate face having a dimensional area which corresponds to said cross section, said flow inlets being in flow communication with said recursive flow path of a first outer first plate for introducing a fluid flow into said stacked array; and a distal plate positioned adjacent said stacked array, said distal plate, defining a final flow path, positioned in flow communication with said recursive flow path in a second outer first plate, said distal plate having a plate face which defines an outlet for fluid exiting said system.

12. The flow system of claim 11 further comprising arranging successive said generations of structural flow channels at different distances from said inlets in the direction of said outlet, whereby to avoid intersection of recursive flow channels.

* * * * *